United States Patent
Bauer et al.

(10) Patent No.: US 10,458,948 B2
(45) Date of Patent: Oct. 29, 2019

(54) MAGNETO-MECHANICAL SENSOR FOR PARAMAGNETIC OXYGEN MEASUREMENT

(71) Applicant: ABB Schweiz AG, Baden (CH)

(72) Inventors: Thomas Bauer, Bad Homburg (DE); Anton Hardock, Offenbach (DE); Eginhard Mueller, Hofheim (DE); Sebastian Maurer, Karben (DE); Francis Rat, Ransbach-Baumbach (DE); Nico Marquart, Freiburg (DE)

(73) Assignee: ABB SCHWEIZ AG, Baden (CH)

( * ) Notice: Subject to any disclaimer, the term of this patent is extended or adjusted under 35 U.S.C. 154(b) by 0 days.

(21) Appl. No.: 15/186,584

(22) Filed: Jun. 20, 2016

(65) Prior Publication Data

US 2016/0299105 A1  Oct. 13, 2016

Related U.S. Application Data

(63) Continuation of application No. PCT/EP2014/003367, filed on Dec. 16, 2014.

(51) Int. Cl.
| | |
|---|---|
| *G01N 27/74* | (2006.01) |
| *G01N 27/76* | (2006.01) |
| *G01N 33/00* | (2006.01) |

(52) U.S. Cl.
CPC ............. *G01N 27/74* (2013.01); *G01N 27/76* (2013.01); *G01N 33/0036* (2013.01)

(58) Field of Classification Search
CPC ..... G01N 27/74; G01N 27/76; G01N 33/0036
USPC ........................................................ 73/25.02
See application file for complete search history.

(56) References Cited

U.S. PATENT DOCUMENTS

| | | | | |
|---|---|---|---|---|
| 3,815,018 A | * | 6/1974 | Gast ...................... | G01N 27/74 324/201 |
| 3,826,974 A | * | 7/1974 | Kocache ................ | G01N 27/74 324/201 |
| 4,347,748 A | * | 9/1982 | Pierson .................... | G01L 3/12 73/862.28 |
| 4,489,596 A | | 12/1984 | Linder et al. | |
| 4,983,913 A | * | 1/1991 | Krause .................. | G01N 27/74 324/204 |
| 5,932,794 A | * | 8/1999 | Fabinski ................ | G01N 27/74 324/204 |
| 6,263,722 B1 | * | 7/2001 | Fabinski ................ | G01N 27/74 324/201 |
| 8,424,388 B2 | * | 4/2013 | Mattes ................. | A61B 5/0215 600/485 |

(Continued)

FOREIGN PATENT DOCUMENTS

| | | |
|---|---|---|
| CN | 101059458 A | 10/2007 |
| CN | 102636558 A | 8/2012 |

(Continued)

*Primary Examiner* — Marrit Eyassu
(74) *Attorney, Agent, or Firm* — Leysig, Voit & Mayer, Ltd.

(57) ABSTRACT

A magneto-mechanical sensor can be use for paramagnetic gas analysis, in which a test piece has a conductor loop is rotatably held by at least one suspension wire. In order to be able to produce the conductor loop, which is to be electrically connected to the at least one suspension wire, with little manual effort and use a small-sized, light-weight sensor, portions of the conductor loop are applied to the surface of the test piece using a metallization process.

7 Claims, 1 Drawing Sheet

(56) References Cited

U.S. PATENT DOCUMENTS

| | | | | |
|---|---|---|---|---|
| 2002/0075007 A1* | 6/2002 | Vogel | .................... | G01N 27/74 |
| | | | | 324/464 |
| 2005/0079684 A1* | 4/2005 | Chong | ................ | B81C 1/00269 |
| | | | | 438/455 |
| 2005/0250231 A1* | 11/2005 | Jen | ..................... | G02F 1/13394 |
| | | | | 438/30 |
| 2008/0223117 A1* | 9/2008 | Watanabe | .............. | B82Y 35/00 |
| | | | | 73/105 |
| 2011/0304322 A1 | 12/2011 | Kovacich et al. | | |
| 2012/0203529 A1 | 8/2012 | Gaskin et al. | | |

FOREIGN PATENT DOCUMENTS

| | | | |
|---|---|---|---|
| DE | 102006021308 | A1 | 10/2007 |
| DE | 102007028148 | A1 | 12/2008 |

\* cited by examiner

MAGNETO-MECHANICAL SENSOR FOR PARAMAGNETIC OXYGEN MEASUREMENT

CROSS-REFERENCE TO RELATED APPLICATIONS

This application is a bypass continuation of PCT/EP2014/003367, filed on Dec. 16, 2014, and claims benefit to German Patent Application No. DE 10 2013 022 015.7, filed on Dec. 20, 2013, each of which is incorporated by reference in its entirety herein. The International Application was published in German on Jun. 25, 2015, as WO 2015/090559 A1 under PCT Article 21(2).

FIELD

The present invention relates to a magneto-mechanical sensor for paramagnetic gas analysis.

BACKGROUND

The field of application of the invention includes paramagnetic gas analysis, in particular oxygen measurement. In this type of measurement, the property of oxygen that is rare in gases is used whereby oxygen has a high paramagnetic susceptibility. If there is an inhomogeneous magnetic field in a gas mixture, the oxygen molecules move along rising field gradients and thus collect in the regions with high field intensities. In order to make this behavior of the oxygen visible, a dumbbell-shaped test piece is used, which is rotatably suspended in a gas in which there is a suitable inhomogeneous magnetic field. By means of the local compression of the paramagnetic oxygen molecules, a torque is exerted on the dumbbell-shaped test piece, which as a result rotates about the axis defined by the at least one tensioning wire, preferably through the centroid of the test piece. To measure said movement precisely, a mirror is used as part of a light balance, which measures the deviation of a light reflection from said mirror onto a photo sensor. In order to compensate for the movement of the test piece, a current is conducted through the conductor loop, which current interacts with the magnetic field and guides the test piece back into its resting position. The intensity of said current is then a measurement for the oxygen concentration.

It is known from DE 10 2006 021 308 B4 to vapor-deposit the conductor loop onto the surface of the test piece of a paramagnetic oxygen analyzer. In said prior art, the test piece is retained by an arrangement of springs that are situated in a planar manner in a plane together with the rotational plane of the test piece. Therefore, it is possible that the conductor loop is attached only on one side of the test piece, generally the upper side, and is galvanically connected to the springs, which conduct the current in order to generate the torque.

In an arrangement such as that in the preamble of said invention in which a test piece is rotatably retained by at least one tensioning wire, said configuration is, however, not possible since the tensioning wire is not situated in a planar manner in a plane together with the rotational plane of the test piece, but is largely perpendicular to said plane. There is therefore a need for an electrical line, which can also be part of the conductor loop, from the upper side to the lower side of the test piece, since the current is in this case conducted further to close the circuit. The technically certainly obvious vapor deposition of an electrical line over an edge and over a thin outer surface that would be required to guide a continuous conductor loop over a plurality of side surfaces of the test piece appears to be impractical, however.

SUMMARY

An aspect of the invention provides a magneto-mechanical sensor for paramagnetic gas analysis, the sensor comprising: a dumbbell-shaped test piece configured for rotatable suspension in an inhomogeneous magnetic field; an electrically conductive tensioning wire, which is attached coaxially to an axis of rotation of the test piece for the rotatable suspension thereof; a conductor loop, attached to the test piece, configured to generate a torque thereby stabilizing the test piece during energizing in interaction with the inhomogeneous magnetic field; and a mirror arranged on the test piece as a component of a visual set of scales, configured to measure a deflection of the test piece, wherein at least part of the conductor loop, galvanically connected to the tensioning wire, is applied to a surface of the test piece using metallization.

BRIEF DESCRIPTION OF THE DRAWINGS

Further features that improve the invention are described in more detail below together with the description of a preferred embodiment of the invention on the basis of the drawings, in which.

DETAILED DESCRIPTION

Figure 1:
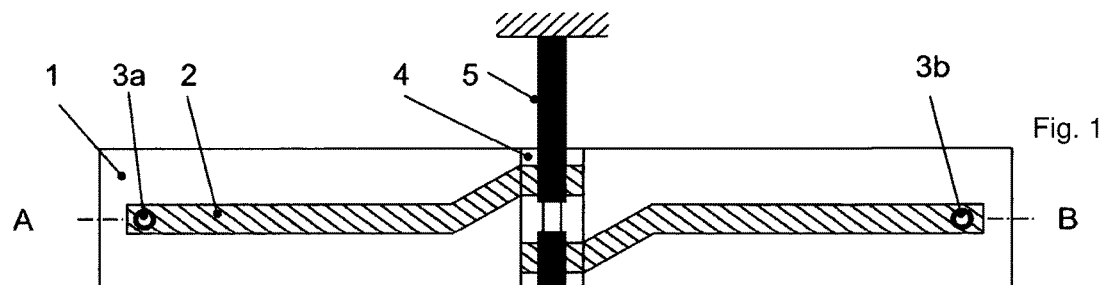
FIG. 1 is a view of the front side of a sensor according to the invention according to a first embodiment.

One advantage of depositing electrical lines by metallization instead of for example by soldering on wires is that a surface can easily be metallized automatically, without or with little manual human handling, for example by physical vapor deposition (PVD) or chemical vapor deposition (CVD). Furthermore, any method for miniaturizing the test piece is desirable, since smaller, more compact and lighter test pieces react to the introduction of force in a more sensitive manner because of their low mass. Furthermore, the gas to be measured can flow around said test pieces in smaller chambers, which minimizes delay by means of which a sensor of this type reacts to changes in the oxygen content in the gas to be measured, since less gas has to be supplied in order to fill the surrounding volume. By supplying the gas to be measured more quickly, minimizing said delay is only possible to a limited extent since the sensor can be deflected by the associated particulate flow.

An aspect of the present invention relates to a magneto-mechanical sensor for paramagnetic gas analysis, comprising a dumbbell-shaped test piece for rotatable suspension in an inhomogeneous magnetic field, at least one electrically conductive tensioning wire, which is attached coaxially to the axis of rotation of the test piece for the rotatable suspension thereof, a conductor loop attached to the test piece, in order to generate a torque for stabilizing the test piece during energizing in interaction with the inhomogeneous magnetic field, and a mirror arranged on the test piece as a component of a visual set of scales, for measuring a deflection of the test piece.

An aspect of the invention provides a magneto-mechanical sensor in which the conductor loop provided for galvanic connection to a tensioning wire can be produced with low production expenditure, is small is size and has a low weight.

An aspect of the invention includes the technical teaching that at least parts of the conductor loop are applied to the surface of the test piece by means of metallization. In this case, the metallization can be carried out using different thin layer technology, including vapor deposition by PVD, for example by sputtering, and by CVD.

In this case, it is advantageous that, inter alia, lower production costs can be achieved, as well as high sensitivity and low response times of the sensor to changes for example in the oxygen content in the gas to be measured, since the test piece together with the conductor loop can be produced to have a low weight and small dimensions.

According to a feature that improves the invention, it is proposed that plated through-holes are provided in the test piece, which enable the line of electric current to pass from one side of the test piece to the opposite side. In this way, the conductor loop can be produced in full by combining a vapor-deposited part and at least one plated through-hole. The working steps required for production, i.e. vapor deposition and producing the plated through-holes, can be carried out without manual human handling.

According to another feature that improves the invention, it is proposed to provide a three-dimensional structure on the test piece in the region of its centroid, which structure enables a partial or complete positive connection to an end piece of at least one tensioning wire. Such a suitable structure can then be used as a guide when the tensioning wire is fastened to the test piece, in order to minimize the distance from the axial axis of the tensioning wire to the centroid of the test piece and in order to simplify the manual fastening of the tensioning wire to the test piece and in order to reduce to amount of time required for this purpose.

According to a preferred embodiment of the invention, it is proposed to likewise vapor-deposit the mirror, the mirror also being able to be produced as part of the vapor-deposited part of the conductor loop. This simplifies the production process.

In addition, the tensioning wire can be attached to the vapor-deposited part of the conductor loop by soldering, by joining using conductive adhesive or by bonding, depending on the condition of the components to be joined. In this way, the mechanical and galvanic connection of the tensioning wire and the conductor loop is performed in one working step.

In a preferred embodiment of the invention, it is proposed for the test piece to be solid. For production, the test piece can thus be stamped or cut from a substrate for example. An alternative to this construction consists for example in a hollow test piece, which can be filled with a diamagnetic gas for example.

FIG. 1 shows the front side of a test piece 1, comprising a part of the vapor-deposited conductor loop 2, a tensioning wire 5 fastened thereto by soldering tin (not shown), a three-dimensional structure 4 in partial positive connection to an end piece of the tensioning wire 5 and the outlets of two plated through-holes 3a, 3b. In this case, the positive connection is made by a cylindrical recess in the test piece 1 that is trapezoidal in cross section and enables only one degree of freedom towards the axis of rotation of the test piece 1 when the attached tensioning wire 5 is positioned on the test piece 1 manually or mechanically, said degree of freedom being insignificant for coaxially fastening the tensioning wire 5 to the test piece 1. The accuracy of the positioning of the tensioning wire 5 is thereby increased, while the time required for positioning is reduced.

Figure 2:
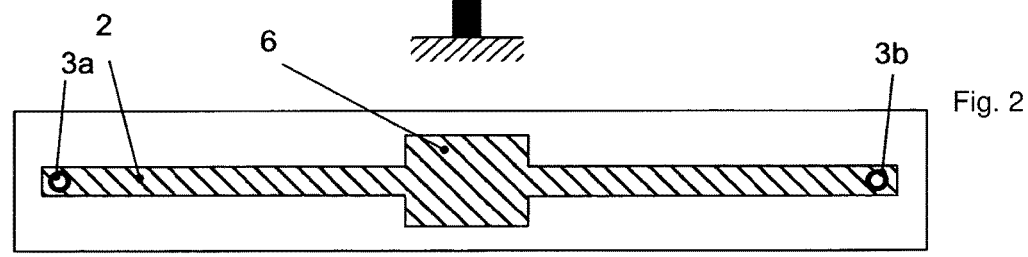
FIG. 2 is a view of the rear side thereof.

FIG. 2 shows the rear side of the test piece 1, comprising another part of the conductor loop 2 and a mirror 6 that is designed as part of the conductor loop. This part of the conductor loop 2 is galvanically connected to the part shown in FIG. 1 by the two plated through-holes 3a, 3b.

Figure 3:
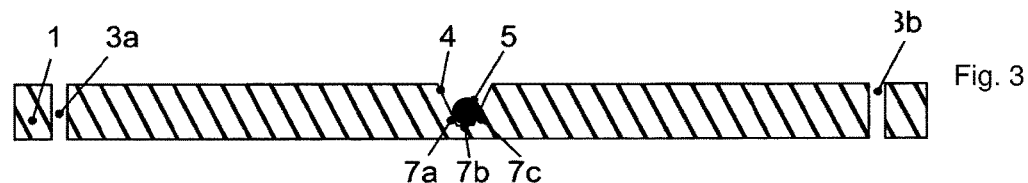
FIG. 3 is an A-B section according to FIG. 1.

FIG. 3 shows the two plated through-holes 3a, 3b and the cross section through the cylindrical recess. This shape makes it possible for a secure positive connection and galvanic contact to be made to a tensioning wire 5 that is circular in cross section on contact lines 7a, 7b, 7c. This ensures improved mechanical and galvanic connection compared with contacting with only one contact line, as would be the case without the three-dimensional structure 4. At the same time it can be seen that the wire cannot be moved laterally away from the centroid of the test piece because of the three-dimensional structure 4, which simplifies the attachment of the wire in the construction of the sensor.

Figure 4:
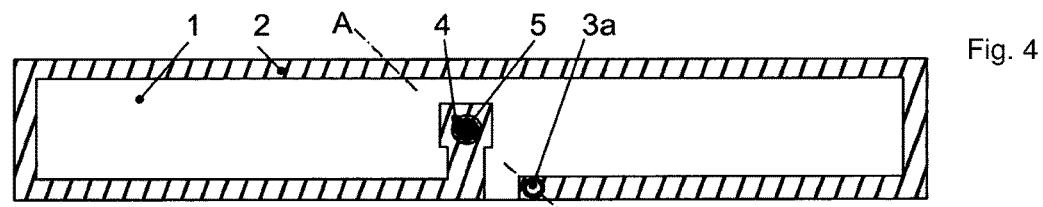
FIG. 4 is a view of the top side of a sensor according to the invention according to another embodiment.

Another embodiment according to the invention is shown in FIG. 4. Said figure shows the upper side of a test piece 1 comprising a tensioning wire 5 that is coaxial with the axis of rotation of the test piece, a conductor loop 2 that is vapor-deposited in the form of a wrapping around the axis of rotation, a plated through-hole 3a and a hole 4 for positive connection to the end piece of the tensioning wire 5. The plated through-hole 3a galvanically connects the upper side of the test piece to the lower side thereof.

Figure 5:
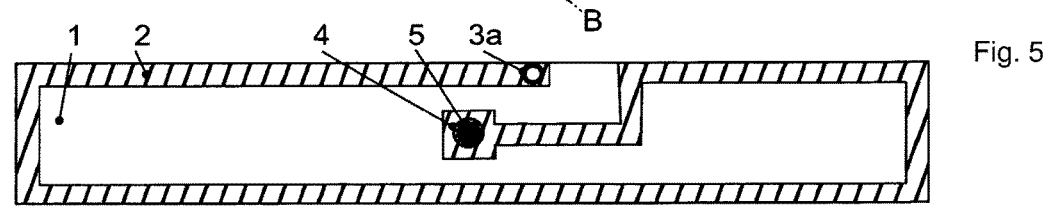
FIG. 5 is a view of the rear side thereof.

FIG. 5 shows the lower side. It can be seen here that another part of the conductor loop 2 is in the form of a wrapping around the axis of rotation of the test piece 1, in the same rotational direction as on the upper side, such that the magnetic field that is generated by a current in the conductor loop on the upper side is oriented in the same way as the magnetic field that is generated on the lower side by the same current that is conducted through the plated through-hole 3a. In addition, because of the multi-layered design, the force which is caused by the current in the conductor loop 2 can thus be increased. The force can be reduced simply by using geometric straight conductor elements, for example, instead of wrappings.

Figure 6:
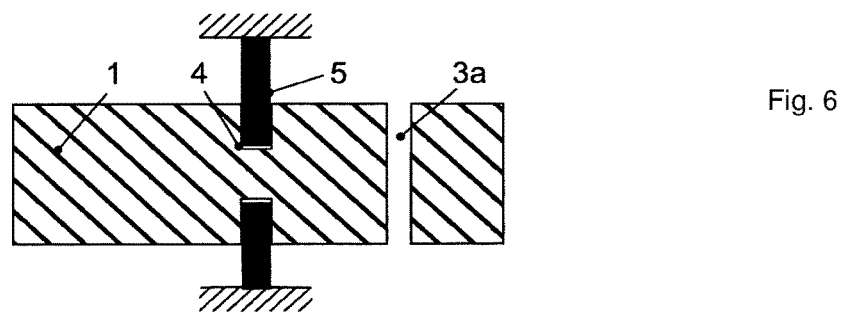
FIG. 6 is an A-B section according to FIG. 3.

FIG. 6 shows the holes 4 which enable a positive connection to the end of the at least one tensioning wire 5. When attaching a tensioning wire, there is still no degree of three-dimensional freedom, as a result of which the speed and the precision of manual construction achieved can be considerably increased.

The invention is not limited to the above-mentioned preferred embodiments. Rather, deviations therefrom are also conceivable that are included in the scope of protection of the claims which follow. Thus, it is also possible, for example, for the conductor loop to be asymmetrically formed on only one arm of the dumbbell-shaped test piece. The three-dimensional structure for positive connection to an end piece of the tensioning wire can also be implemented in the form of a raised portion instead of a recess.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B, and C" should be interpreted as one or more of a group of elements consisting of A, B, and C, and should not be interpreted as requiring at least one of each of the listed elements A, B, and C, regardless of whether A, B, and C are related as categories or otherwise. Moreover, the recitation of "A, B, and/or C" or "at least one of A, B, or C" should be interpreted as including any singular entity from the listed elements, e.g., A, any subset from the listed elements, e.g., A and B, or the entire list of elements A, B, and C.

LIST OF REFERENCE SIGNS 1 test piece
2 conductor loop
3a first plated through-hole
3b second plated through-hole
4 three-dimensional structure on the test piece
5 tensioning wire
6 mirror
7a first contact line
7b second contact line
7c third contact line

The invention claimed is:

1. A magneto-mechanical sensor for paramagnetic gas analysis, the sensor comprising:
   a dumbbell-shaped test piece configured for rotatable suspension in an inhomogeneous magnetic field;
   an electrically conductive tensioning wire, which is attached coaxially to an axis of rotation of the test piece for the rotatable suspension thereof;
   a conductor loop, attached to the test piece, configured to generate a torque thereby stabilizing the test piece during energizing in interaction with the inhomogeneous magnetic field when current is supplied; and
   a mirror arranged on the test piece, configured to measure a deflection of the test piece,
   wherein at least parts of the conductor loop, which are electrically conductively connected to the tensioning wire, are applied to a surface of the test piece using metallization,
   wherein the test piece is solid,
   wherein the mirror is applied to the test piece using metallization, and
   wherein the mirror is part of the conductor loop.

2. The sensor of claim 1, wherein at least part of the conductor loop is in the form of a plated through-hole, configured to establish galvanic contact between one or more parts of the conductor loop and one or more surfaces that are offset in parallel.

3. The sensor of claim 1, wherein at least one structure is stamped on the test piece,
   wherein the structure enables a positive connection to an end piece of the tensioning wire so as to simplify fastening of the tensioning wire.

4. The sensor of claim 1, wherein the tensioning wire is attached to the conductor loop by soldering.

5. The sensor of claim 1, wherein the tensioning wire is attached to the conductor loop by conductive adhesive.

6. The sensor of claim 1, wherein the tensioning wire is attached to the conductor loop by bonding.

7. The sensor of claim 1, comprising two or more of the electrically conductive tensioning wire.

* * * * *